United States Patent
Kalenyak et al.

(10) Patent No.: US 9,154,014 B2
(45) Date of Patent: Oct. 6, 2015

(54) DEVICE FOR ELECTROMAGNETICALLY BEARING AND DRIVING A TILTABLE PART OF A GANTRY OF A COMPUTER TOMOGRAPHY APPARATUS, AND A COMPUTER TOMOGRAPHY APPARATUS EMBODYING SAME

(75) Inventors: Johann Kalenyak, Schesslitz (DE); Hans-Jürgen Müller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 410 days.

(21) Appl. No.: 13/639,072

(22) PCT Filed: Mar. 22, 2011

(86) PCT No.: PCT/EP2011/054286
§ 371 (c)(1),
(2), (4) Date: Oct. 2, 2012

(87) PCT Pub. No.: WO2011/128180
PCT Pub. Date: Oct. 20, 2011

(65) Prior Publication Data
US 2013/0028390 A1    Jan. 31, 2013

(30) Foreign Application Priority Data
Apr. 15, 2010   (DE) .......................... 10 2010 015 062

(51) Int. Cl.
*A61B 6/00*   (2006.01)
*H02K 7/09*   (2006.01)
*A61B 6/03*   (2006.01)
*F16C 32/04*   (2006.01)

(52) U.S. Cl.
CPC   *H02K 7/09* (2013.01); *A61B 6/035* (2013.01); *A61B 6/4441* (2013.01); *F16C 32/04* (2013.01); *F16C 2300/14* (2013.01); *F16C 2316/10* (2013.01)

(58) Field of Classification Search
CPC ............. A61B 6/035; A61B 6/56; H02K 7/09
USPC ...................................................... 378/4, 15
See application file for complete search history.

(56) References Cited

U.S. PATENT DOCUMENTS

| | | | |
|---|---|---|---|
| 4,099,059 A | | 7/1978 | Distler |
| 4,541,108 A | | 9/1985 | Grady et al. |
| 4,723,259 A | * | 2/1988 | Amor et al. ..................... 378/10 |
| 4,729,259 A | | 3/1988 | Lanzer |
| 5,438,605 A | * | 8/1995 | Burke et al. .................. 378/135 |
| 5,475,729 A | | 12/1995 | Mattson et al. |
| 5,548,629 A | | 8/1996 | Kimura et al. |

(Continued)

FOREIGN PATENT DOCUMENTS

| | | | |
|---|---|---|---|
| EP | 0549912 A1 | * | 7/1993 |
| EP | 0676911 A1 | | 10/1995 |

(Continued)

*Primary Examiner* — Michael Maskell
(74) *Attorney, Agent, or Firm* — Schiff Hardin LLP

(57) ABSTRACT

A device for mounting and driving a tiltable part of a gantry of a computed tomography system with respect to a pedestal of the gantry around a system axis of the pedestal, has a magnetic bearing that magnetically supports the tiltable part relative to the pedestal, and an electromagnetic drive that electromagnetically tilts the tiltable part of the gantry relative to the pedestal.

50 Claims, 4 Drawing Sheets

(56) References Cited

U.S. PATENT DOCUMENTS

| | | | |
|---|---|---|---|
| 5,799,054 A | 8/1998 | Hum et al. | |
| 6,453,004 B1 * | 9/2002 | Albeniz et al. | 378/62 |
| 6,609,826 B1 | 8/2003 | Fujii et al. | |
| 2004/0062343 A1 | 4/2004 | Brunnett et al. | |
| 2005/0063709 A1 | 3/2005 | Poisel et al. | |
| 2005/0116558 A1 * | 6/2005 | Yokoyama et al. | 310/68 B |
| 2007/0230654 A1 | 10/2007 | Chappo et al. | |
| 2007/0274436 A1 | 11/2007 | Harada et al. | |
| 2009/0308285 A1 | 12/2009 | Bode et al. | |
| 2011/0158382 A1 | 6/2011 | Sahin Nomaler et al. | |

FOREIGN PATENT DOCUMENTS

| | | | |
|---|---|---|---|
| WO | 2010026523 A2 | 3/2010 | |
| WO | WO 2010026523 A2 * | 3/2010 | F16C 39/06 |
| WO | WO 2010/079392 A1 | 7/2010 | |

* cited by examiner

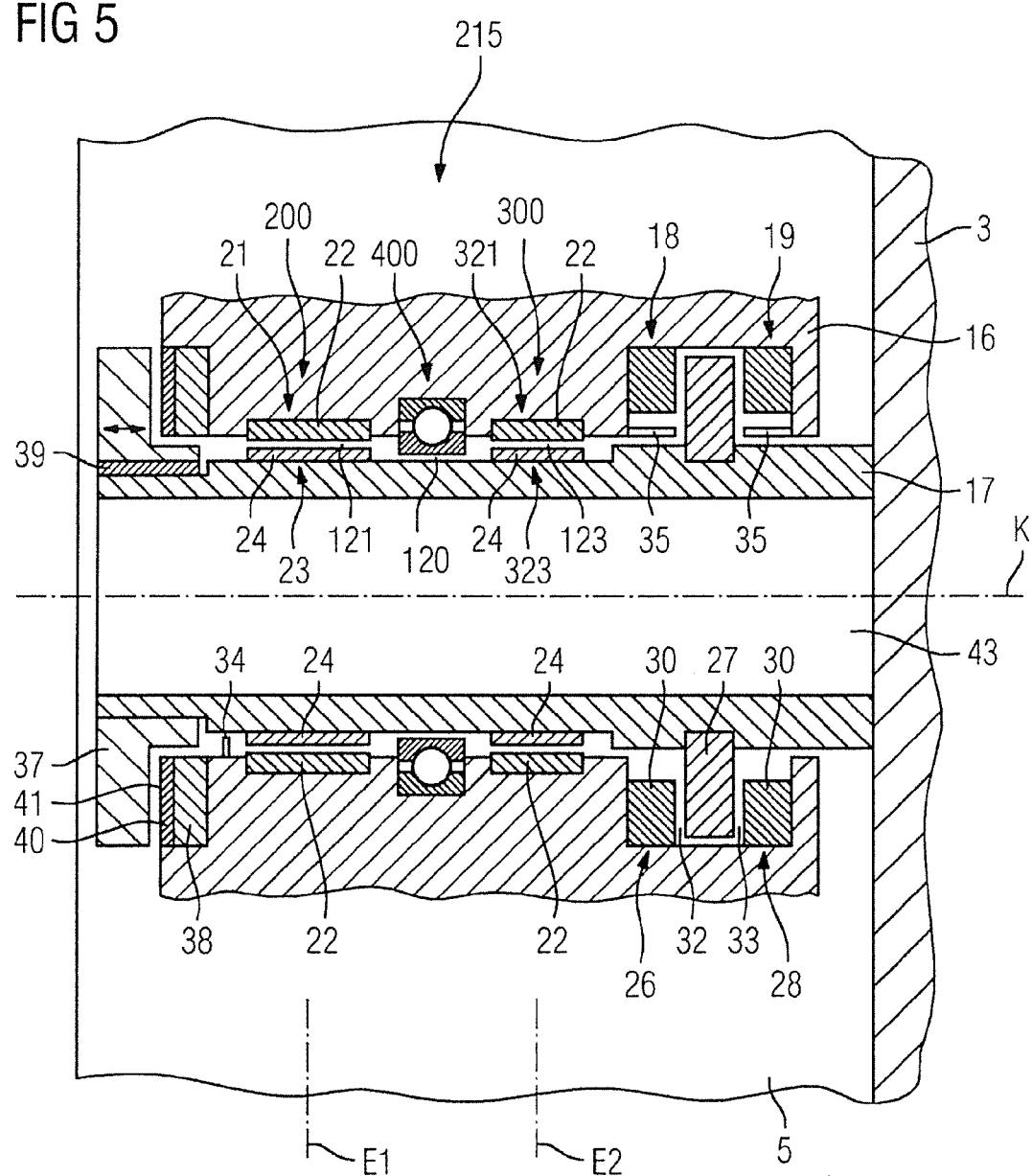

DEVICE FOR ELECTROMAGNETICALLY BEARING AND DRIVING A TILTABLE PART OF A GANTRY OF A COMPUTER TOMOGRAPHY APPARATUS, AND A COMPUTER TOMOGRAPHY APPARATUS EMBODYING SAME

BACKGROUND OF THE INVENTION

1. Field of the Invention

The invention concerns a device for bearing and driving a part, tiltable on a tilt axis, of a gantry of a computed tomography apparatus—which gantry has the tilt axis—relative to a pedestal of the gantry of the computed tomography apparatus. The invention also concerns a computed tomography apparatus that embodies such a device.

2. Description of the Prior Art

Computed tomography apparatuses of the third generation have a gantry with a stationary part and a part that can be rotated relative to the stationary part, around a system axis of the gantry. The rotatable part has the shape of a drum on which are arranged the components of the computed tomography apparatus (such as the x-ray source, the x-ray detector, a control system, etc.) that rotate around a patient arranged along the system axis in a measurement field during operation of the computed tomography apparatus. Given a system with only one x-ray source and one x-ray detector, a completely populated drum reaches a mass of approximately 800 kg to 900 kg and rotates with a rotation speed of up to 240 R/min during operation.

For specific examinations it is necessary to tilt or pivot the x-ray system around a tilt axis that is at a right angle to the system axis, the tilt angle essentially proceeding horizontally. The tilt angle amounts to at most +/−30° out of the starting position. The rotatable part and the stationary part of the gantry are normally tilted relative to a pedestal of the gantry. The tilting must be able to occur exactly, precise to a minute of a degree. Presently, roller bearings or slide bearing bushings are used to support the stationary and rotatable part relative to the pedestal of the gantry. Such roller bearings or slide bearing bushings are subject to a certain wear and must be regularly serviced (re-oiled, for example). For example, the drive comprises a motor interacting with a worm gear.

SUMMARY OF THE INVENTION

An object of the invention is to provide a device and a computed tomography apparatus of the aforementioned type such that the bearing and the drive of a part of the gantry of the computed tomography apparatus, which part can be tilted around a tilt axis relative to a pedestal of said gantry of the computed tomography apparatus, is improved.

The above object is achieved in accordance with the present invention by a device for supporting and driving a tiltable part of a computed tomography apparatus gantry with respect to a pedestal of the gantry, the pedestal having a tilt axis. The device includes an electromagnetic bearing that supports the tiltable part of the gantry relative to the pedestal, and an electromagnetic drive that electromagnetically tilts the tiltable part of the gantry relative to the pedestal.

Due to the magnetic bearing of the tiltable part of the gantry relative to the pedestal of said gantry, mechanical contact no longer occurs between bearing parts. The magnetic bearing is friction-free and wear-free, such that a re-oiling or a re-greasing as in roller bearings is not necessary.

The electromagnetic drive that tilts the tiltable part of the gantry relative to the pedestal of the gantry, and the magnetic bearing that supports the tiltable part of the gantry relative to the pedestal of the gantry, are advantageously combined into one unit (in particular a structural unit).

According to one variant of the invention, the magnetic bearing is formed by at least one radial bearing and at least one axial bearing in relation to the tilt axis.

According to a further variant of the invention, the magnetic bearing has at least one permanent magnet, at least one electromagnet having a coil and/or at least one element made of a ferromagnetic material, and the electromagnetic drive has at least one electromagnet having a coil. In principle, the magnetic bearing can be realized as a purely passive magnetic bearing with a corresponding arrangement of permanent magnets and elements made of a ferromagnetic material on the tiltable part and the pedestal of the gantry relative to one another, with either the repulsive and attractive forces occurring between permanent magnets or the attractive forces between permanent magnets and ferromagnetic materials being utilized. However, to stabilize the magnetic bearing the radial and axial bearings preferably also have electromagnets including coils in order to be able to modify the magnetic field (and therefore the currently acting forces in the respective magnetic bearings) by variation of the currents flowing through the coils or electromagnets. For this, a corresponding regulation is required that ensures that the necessary bearing forces are provided.

The electromagnets (normally having multiple, or at least one coil) of the electromagnetic drive are necessary to generate a rotating electromagnetic field to tilt the tiltable part relative to the pedestal of the gantry, and for this purpose, must be controlled accordingly. The electromagnetic drive can also have permanent magnets and/or elements made of a ferromagnetic material.

According to one embodiment of the invention, the radial bearing and/or the electromagnetic drive has a first, radially outward, annular radial arrangement of permanent magnets, electromagnets and/or elements made of a ferromagnetic material, which arrangement is associated with the pedestal of the gantry, and a second, radially inward, annular radial arrangement of permanent magnets, electromagnets and/or elements made of a ferromagnetic material, which arrangement is associated with the tiltable part of the gantry. An annular radial bearing gap is located between the first and second annular radial arrangement.

According to a further embodiment of the invention, the at least one axial bearing has at least one first annular axial arrangement of permanent magnets, electromagnets and/or elements made of a ferromagnetic material, which first arrangement is associated with the pedestal of the gantry, and at least one second, annular axial arrangement of permanent magnets, electromagnets and/or elements made of a ferromagnetic material, which at least one second arrangement is associated with the tiltable part of the gantry. In either or both at least one first and at least one second axial arrangement, the annular element made of a ferromagnetic material forms an annular axial bearing gap, the gaps being axially offset relative to one another in the direction of the tilt axis.

A variant of the invention provides that the device or the structural unit embodying the magnetic bearing and the electromagnetic drive has a measurement system to determine the change of the width of the annular radial bearing gap and/or of the annular axial bearing gap. In order to be able to realize a functional and interference-free magnetic bearing, the widths of the bearing gaps must be kept essentially constant. The width of a bearing gap is essentially the control variable in the regulation of the bearing forces. The width is advantageously defined without contact with the measurement means. The width is normally determined at two points of the annular bearing gaps that are offset relative to one another by approximately 90°. Moreover, depending on design, the width of a bearing gap does not always need to be the same over the entire bearing gap. Rather, the bearing gap can have a manner of profile so that different widths of the bearing gap result at different points of the bearing gap. In such a case, the width of the bearing gap at a defined location of said bearing gap is respectively determined and used for regulation.

The measurement system can have at least one Hall sensor and/or one sensor operating inductively or capacitively.

According to a variant of the invention, if electromagnets are used for the magnetic bearing, the determination of the change of the width of the radial bearing gap and/or of the axial bearing gap takes place based on the effect of the inductivity of the coil of one or more electromagnets. For example, a position change of the inward radial arrangement of permanent magnets, electromagnets and/or elements made of a ferromagnetic material of the tiltable part of the gantry relative to the outward radial arrangement affects the inductivities of the electromagnets of the outward radial arrangement. Current and voltage values thereby change at the electromagnets of the outward radial arrangement, which changes are evaluated to determine the width of the respective bearing gap.

In an embodiment of the invention the radial bearing is arranged in a first plane, and the electromagnetic drive is arranged in a second plane that is offset relative to the first plane in the direction of the tilt axis.

In another embodiment of the invention the electromagnetic drive is integrated into the radial bearing.

According to a first such variant of the integration, the first, radially outward, annular radial arrangement has electromagnets and the second, radially inward, radial arrangement has permanent magnets and/or elements made of a ferromagnetic material, and a group of electromagnets of the first radial arrangement is controlled such that a rotating electromagnetic field is generated to electromagnetically tilt the tiltable part of the gantry.

According to a second such variant of the integration, the first, radially outward, annular radial arrangement has permanent magnets and/or elements made of a ferromagnetic material and the second, radially inward, radial arrangement has electromagnets, and a group of electromagnets of the second radial arrangement is controlled such that a rotating electromagnetic field is generated to electromagnetically drive the tiltable part of the gantry.

According to a further variant of the invention, the first, radially outward annular radial arrangement and the second, radially inward annular arrangement have electromagnets, and a group of electromagnets of the first and/or the second radial arrangement is controlled such that a rotating electromagnetic field is generated to electromagnetically drive the tiltable part of the gantry.

In a further embodiment of the invention, the electromagnets of the first and/or the second radial arrangement that are provided for electromagnetic driving and/or for magnetic bearing are respectively grouped in segments. The electromagnets can respectively be grouped in two or more segments. For example, the electromagnets provided for electromagnetic driving can be grouped into three segments that respectively cover approximately 60° of the radial bearing; which segments are respectively separated from one another by a segment (likewise covering a 60° angle) in which are grouped electromagnets provided for magnetic bearing. Given a four-segment arrangement, the electromagnets provided for electromagnetic driving and the electromagnets provided for magnetic bearing alternately cover a respective 45° angle of the radial bearing, such that four segments are present for the driving and four segments are present for the bearing. Additional segmentations are likewise possible.

In another embodiment of the invention the device has at least one magnetic brake. The magnetic brake has at least one flange that can be moved in the direction of the tilt axis and at least one magnet interacting with this flange. For example, the flange can be of annular design and can be directed via one or more feather keys in the direction of the tilt axis.

In another embodiment of the invention, given tilting movements of the tiltable part of the gantry the flange is held—without being engaged—by the magnetic field of at least one electromagnet (normally by the magnetic fields of multiple electromagnets) of the magnetic brake, such that it does not deploy a braking effect. In contrast to this, to fix the tiltable part of the gantry the flange interacts with the radial bearing and/or with the electromagnetic drive such that said flange is pressed against a braking surface by the magnetic field of at least one permanent magnet, normally by the magnetic fields of multiple permanent magnets of the radial bearing and/or the electromagnetic drive.

In a further embodiment of the invention the device or the structural unit has a roller bearing as a support bearing. In the case of a power failure, the support bearing takes over the support function so that damage to the device is avoided.

Alternatively or additionally, an uninterruptible power supply (UPS) can be associated with the device.

The above object also is achieved in accordance with the invention by a computed tomography apparatus having at least one device described in the preceding.

BRIEF DESCRIPTION OF THE DRAWINGS

FIG. 5 is a sectional view of a bearing and drive unit of the computed tomography apparatus of FIG. 1, in a further embodiment of the invention.

DESCRIPTION OF THE PREFERRED EMBODIMENTS

Figure 1:
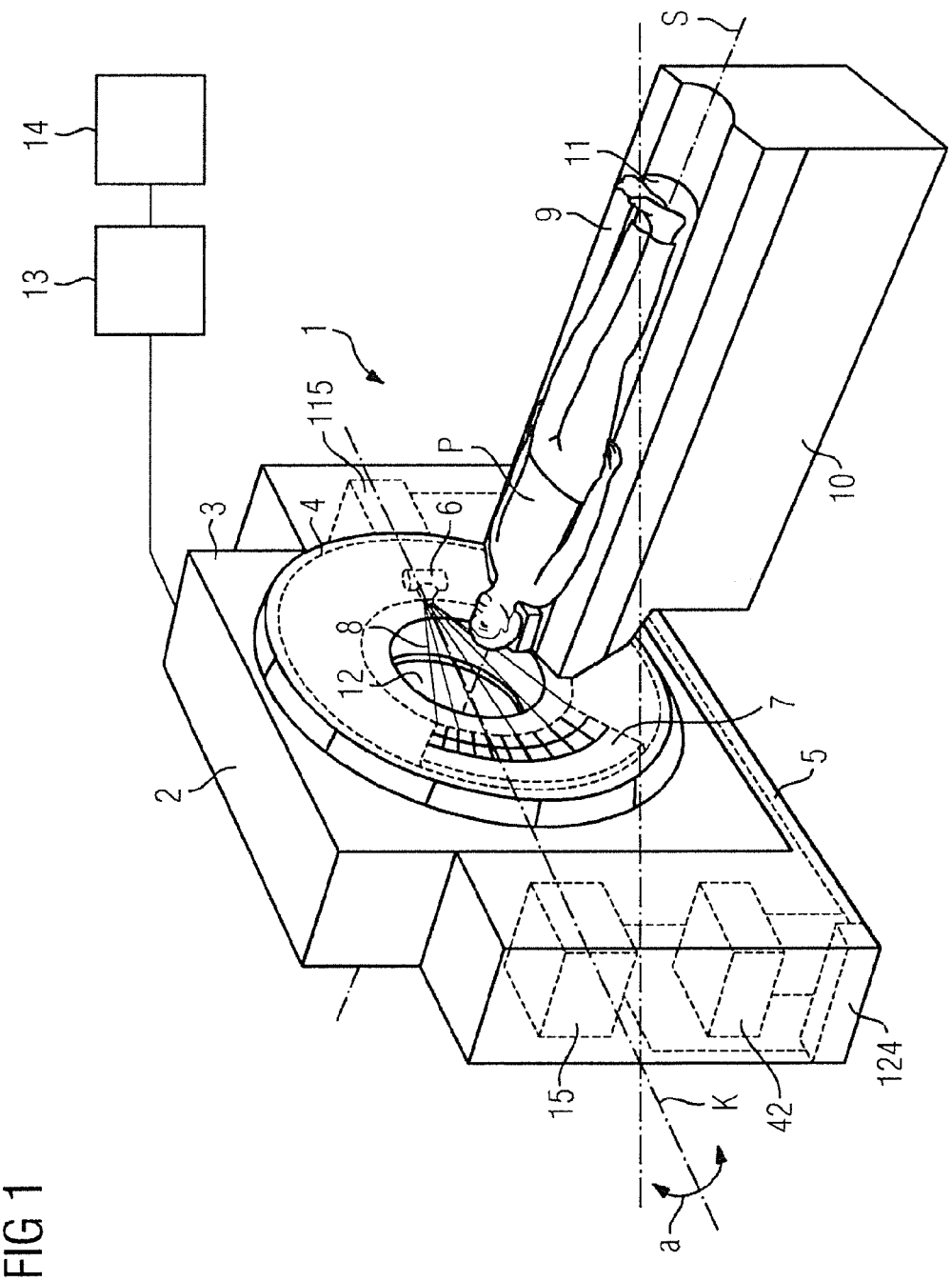
FIG. 1 schematically illustrates a computed tomography apparatus in accordance with the present invention.

Identical or functionally identical elements in the figures are provided with the same reference characters throughout. The representations in the figures are schematic and not necessarily true to scale. The computed tomography apparatus 1 is discussed in the following without limitation as to generality insofar as is necessary to understand the invention.

The computed tomography apparatus 1 shown in FIG. 1 has a gantry 2 with a stationary part 3 and with a part 4 that can rotate around a system axis S. In the exemplary embodiment of the invention, the rotatable part 4 has an x-ray system that includes an x-ray source 6 and an x-ray detector 7 that are arranged opposite one another on the rotatable part 4. During operation of the computed tomography apparatus 1, x-ray radiation 8 emanates from the x-ray source 6 in the direction of the x-ray detector 7, penetrates a measurement subject and is detected by the x-ray detector 7 in the form of measurement data or measurement signals.

Furthermore, the computed tomography apparatus 1 has a patient bed 9 to support a patient P to be examined. The patient bed 9 has a bed base 10 on which a patient support plate 11 is provided to actually support the patient P. The patient support plate 11 is adjustable relative to the bed base 10 in the direction of the system axis S such that it—together with the patient P—can be introduced into the opening 12 of the gantry 2 to acquire 2D x-ray projections of the patient P, for example in a spiral scan. The computational processing of the 2D x-ray projections that are acquired with the x-ray system or, respectively, the reconstruction of slice images, 3D images or a 3D data set based on the measurement data or the measurement signals of the 2D x-ray projections takes place with an image computer 13 of the computed tomography apparatus 1, which slice images or 3D images can be presented at a display device 14.

In the exemplary embodiment of the invention, the gantry 2 also has a pedestal 5 on which the stationary part 3 and the rotatable part 4 of the gantry 2 are mounted. The stationary part 3 and the rotatable part 4 of the gantry 2 can be tilted or pivoted together on a tilt axis K in the directions of the double arrow a, relative to the pedestal 5. The tilt axis K of the gantry 2 is oriented at a right angle to the system axis S and proceeds essentially horizontally. In order to be able to tilt the stationary part 3 and the rotatable part 4 of the gantry 2 around the tilt axis K relative to the pedestal 5, a bearing and drive unit 15 (schematically indicated in FIG. 1) is arranged on at least one side in the pedestal 5.

Figure 2:
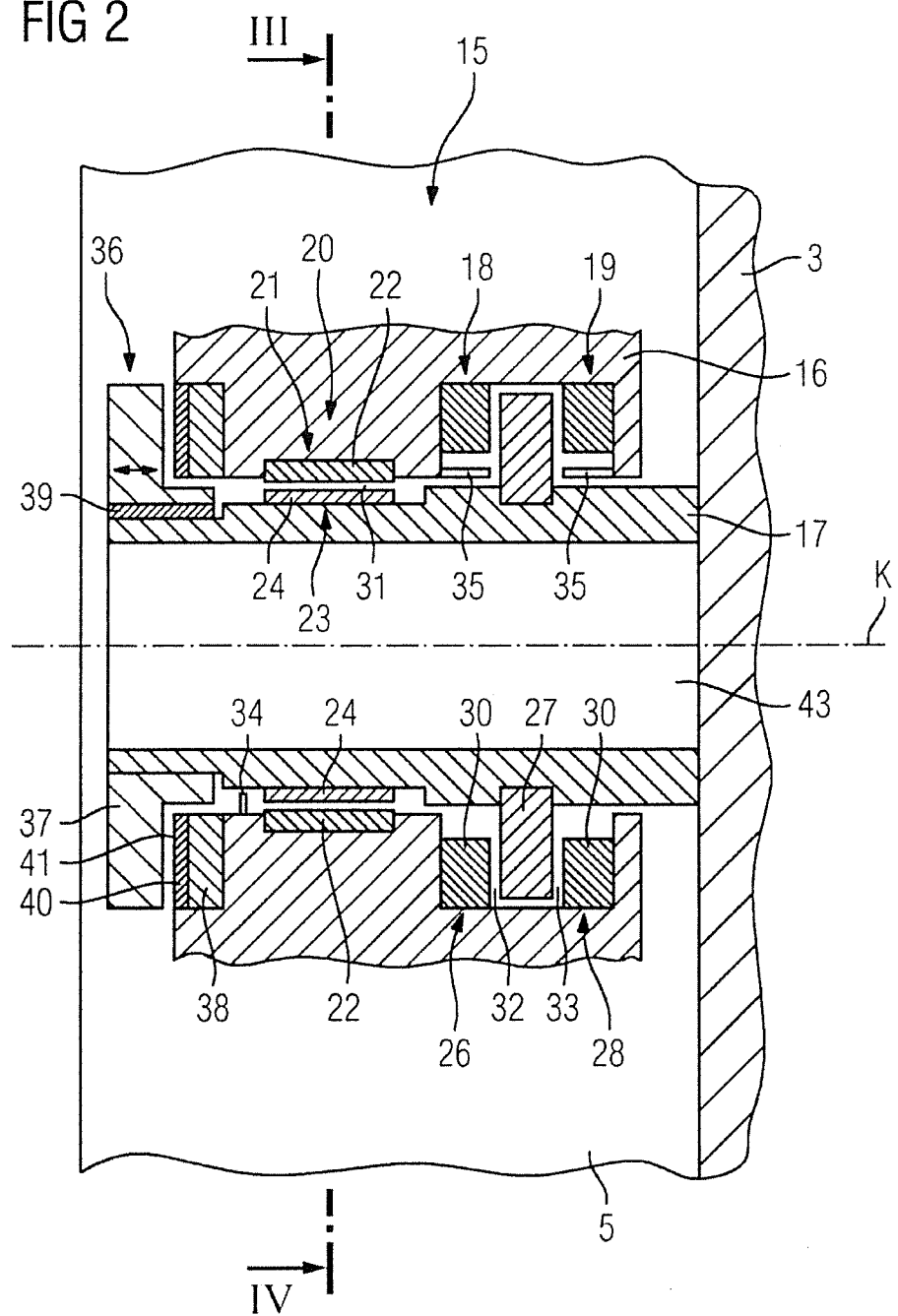
FIG. 2 is a section through a first embodiment of a bearing and drive unit according to the present invention.

One embodiment of such a bearing and drive unit 15 which has a magnetic bearing that supports the stationary part 3 and an electromagnetic drive that tilts the stationary part 3 and the rotatable part 4 relative to the pedestal 5 is schematically illustrated in a sectional view in FIG. 2. The magnetic bearing and the electromagnetic drive can in principle include permanent magnets, electromagnets and/or elements made of a ferromagnetic material.

In the exemplary embodiment of the invention, the bearing and drive unit 15 has a first annular support element 16 is arranged at the pedestal 5 and a second annular support element 17 that is arranged at a bearing axle 43 of the stationary part 3. The bearing axle 43 is permanently connected with the stationary part 3. A second such bearing axle is located on the opposite side of the stationary part 3 (not shown). The tilt axis K runs through both bearing axles (among other things).

The components of the magnetic bearing and the electromagnetic drive are arranged on the annular support elements 16, 17, so as to form in the present exemplary embodiment of the invention two magnetic axial bearings 18, 19 and one magnetic radial bearing 20, with the electromagnetic drive integrated into the latter.

Figure 3:
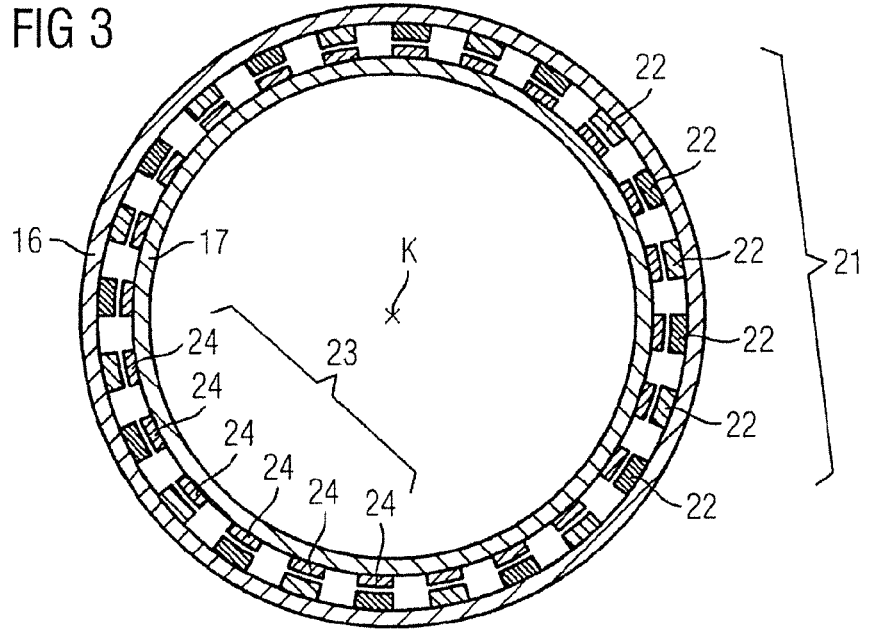
FIG. 3 is a view in the direction of arrows III in the section of FIG. 2, in a first embodiment.

FIG. 3 shows a sectional view through the radial bearing 20 in the direction of the arrows III in FIG. 2. In the exemplary embodiment of the invention that is shown in FIG. 3, the radial bearing 20 and the electromagnetic drive integrated into the radial bearing 20 have a first, radially outward, annular radial arrangement 21 of electromagnets 22 that each include a coil (not shown). Furthermore, the radial bearing 20 and the electromagnetic drive integrated into the radial bearing 20 have a second, radially inward, annular radial arrangement 23 of permanent magnets 24. In the exemplary embodiment of the invention that is shown in FIG. 3, 50% of the electromagnets 22 serve for the magnetic bearing and 50% of the electromagnets 22 serve for the electromagnetic driving of the stationary part 3 and of the rotatable part 4 relative to the pedestal 5. Every other electromagnet 22 of the radially outward, annular radial arrangement 21 is provided to generate a rotating electromagnetic field, which electromagnets 22 are controlled by control unit (not shown in FIG. 3) such that—by interaction with the permanent magnets 24—the stationary part 3 and the rotatable part 4 can be tilted or pivoted relative to the pedestal 5. The remaining electromagnets 22 interact with permanent magnets 24 to produce the magnetic bearing of the stationary part 3 and the rotatable part 4 relative to the pedestal 5. The stationary part 3 and the rotatable part 4 are held in suspension relative to the pedestal 5 as a result of the magnetic fields.

Instead of only the permanent magnets 24, the second radial arrangement can also have elements made of a ferromagnetic material, or permanent magnets and elements made of a ferromagnetic material.

According to an alternative embodiment of the radial bearing 20 integrated with the electromagnetic drive, the radially outward, annular radial arrangement 21 can have elements made of a ferromagnetic material and/or permanent magnets and the radially inward, annular radial arrangement 23 can have electromagnets. As described in the preceding—every other electromagnet is provided to generate a rotating electromagnetic field in order—by interaction with the elements made of a ferromagnetic material and/or the permanent magnets—to set the stationary part 3 and the rotatable part 4 into rotation relative to the pedestal 5 for the tilt movement. The remaining electromagnets, by interaction with the elements made of a ferromagnetic material and/or the permanent magnets, in turn serve for the magnetic bearing of the stationary part 3 and the rotatable part 4 relative to the pedestal 5. In these variants, the electrical energy required for the generation of the rotating field and the control and regulation signals must be transmitted to the stationary part 4 via slip rings, for example.

In an additional alternative embodiment of the radial bearing 20 integrated with an electromagnetic drive, both the radially outward, annular radial arrangement 21 and the radially inward, annular radial arrangement 23 have electromagnets, and at least a portion of the electromagnets of the first and second radial arrangements are provided for the magnetic bearing, and a group of electromagnets of the first and/or second radial arrangement can be controlled such that a rotating electromagnetic field is generated to electromagnetically drive the stationary part 3 and the rotatable part 4 of the gantry 2. In this case, it can also be necessary to transmit the electrical energy required to generate the rotating field and possibly the control and regulation signals to the stationary part 4 via slip rings, for example.

Figure 4:
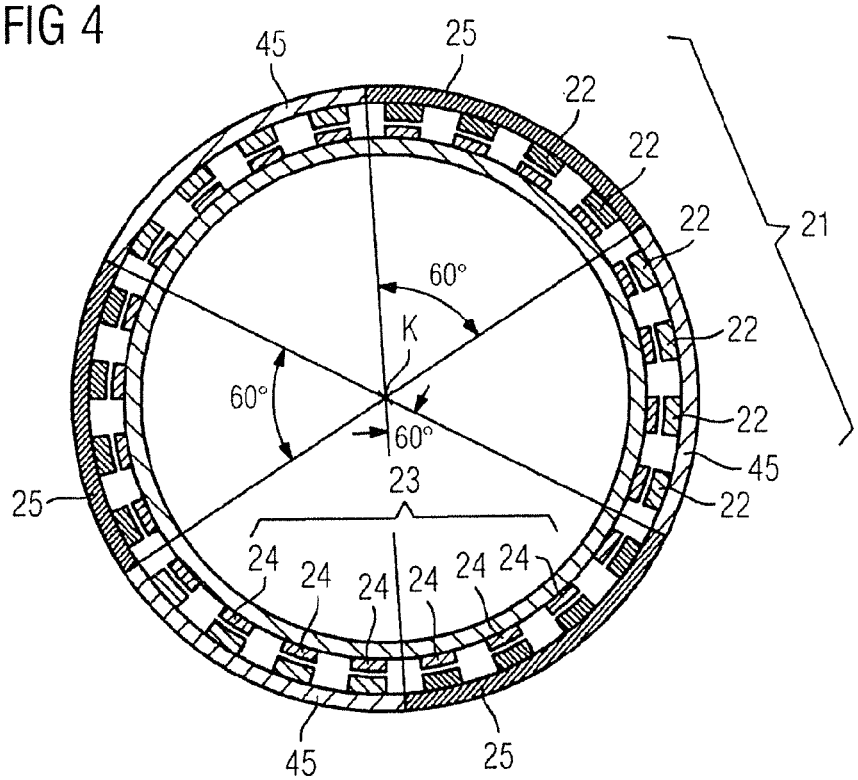
FIG. 4 is a view in the direction of arrows III in the section of FIG. 2, in a second embodiment.

The electromagnets 22 provided for the electromagnetic driving and the electromagnets 22 of the radial bearing 20 that are provided for the magnetic bearing can also be respectively grouped into segments. FIG. 4 shows such a segmentation in a further development of the exemplary embodiment of the invention that is shown in FIG. 3. In the exemplary embodiment of the invention that is shown in FIG. 4, the electromagnets 22 provided for driving are arranged in three segments 25 that respectively cover a 60° angle, wherein a 60° angle is likewise located between each segment 25. The electromagnets 22 that are arranged in these intervening segments 45 are provided for the magnetic bearing. Other segment arrangements with other angles are likewise possible. Such a segmentation is also possible for the described alternative embodiments of the radial bearing integrated with the electromagnetic drive.

As noted, the bearing and drive unit 15 has two axial bearings 18 and 19. In the exemplary embodiment of the invention, the axial bearing 17 has a first annular axial arrangement 26 of electromagnets 30 (and possibly of permanent magnets and/or of elements made of a ferromagnetic material) which are attached to the first annular support element 16 and are associated with the pedestal 5. The electromagnets 22 of the first axial arrangement 26 interact with an annular flange 27 made of a ferromagnetic material, which flange is attached to the support element 17 and is associated with the stationary part 3 and the rotatable part 4.

The design of the axial bearing 19 corresponds to the design of the axial bearing 18. The axial bearing 19 also has a first annular axial arrangement 28 of electromagnets 30 (and possibly of permanent magnets and/or of elements made of a ferromagnetic material) which are attached to the first annular support element 16 and are associated with the pedestal 5. The electromagnets 22 of the first axial arrangement 26 likewise interact with the annular flange 27.

The axial bearings 18 and 19 set the stationary part 3 and the rotatable part 4 into a suspended state in the direction of the tilt axis K, relative to the pedestal 5.

In order to be able to ensure an operation of the magnetic bearings without interference, the width of the radial bearing gap 31 and at least the width of one of the axial bearing gaps 32 and 33 must always be determined. In the case of the present exemplary embodiment of the invention, measurement means are provided for this in the form of Hall sensors. The width of a bearing gap does not need to be determined directly; rather, this can be calculated from the radial or axial position of the annular support element 17. If the width of the bearing gap deviates from its desired width, the width must be adjusted again to the desired width via a corresponding regulation of the coil currents of the electromagnets that are relevant to this. In the case of the present exemplary embodiment of the invention, two Hall sensors 34 (of which two only one is shown in FIG. 2) arranged radially offset from one another by approximately 90° are provided to determine the width of the radial bearing gap 31. Based on the defined and known design of the bearing and drive unit 15, the width of the radial bearing gap 31 can be determined from the measurement values of the Hall sensors 34 by a control and regulation unit and be used to control and regulate the coil currents of the electromagnets relevant to the radial bearing.

The widths of the axial bearing gaps 32 and 33 are determined in a corresponding manner. An arrangement of Hall sensors 35 is shown in FIG. 2. At least two such arrangements of Hall sensors 35, radially offset by approximately 90° relative to one another, are preferably present to acquire measurement values. The width of the axial bearing gap 32 and the width of the axial bearing gap 33 can be determined by a control and regulation unit from the measurement values of the Hall sensors and be used for control and regulation of the coil currents of the electromagnets relevant to the axial bearing.

Alternatively, the determination of the widths of the bearing gap 31 through 33 alternatively takes place with additional sensors via only the evaluation of the changes of current and voltage values of electromagnets. The inductivities of the electromagnets relevant to the magnetic bearing are influenced as a result of a position change of the annular support element 17 relative to the annular support element 16, whereby the current and voltage values at the relevant electromagnets change. The widths of the bearing gaps can respectively be determined via the evaluation of these current and voltage values and be used for the control and regulation of the coil currents of the relative electromagnets.

In the exemplary embodiment shown in FIG. 2, the bearing and drive unit 15 furthermore has a magnetic brake 36. The magnetic brake 36 presently comprises an annular flange 37 made of a ferromagnetic material, which annular flange is movable in the direction of the tilt axis K, and an annular arrangement of electromagnets 38 interacting with the flange 37. The flange 37 is attached to the support element 17 and is thus associated with the stationary part 3. The arrangement of the flange 37 on the support element 17 is such that it is directed in the direction of the tilt axis K via at least one feather key 39 traveling in the direction of the tilt axis K. The electromagnets 38 are arranged on the support element 16 and thus associated with the pedestal 5. A brake ring 40 or a ring 40 with a brake lining 41 is upstream of the electromagnets 38 in the direction towards the flange 37. In the case of the present exemplary embodiment, the magnetic brake 36 is arranged relative to the radial bearing 20 such that the flange 37 is still located in the magnetic field of the permanent magnet 24.

During operation of the bearing and drive unit 15, the radial bearing 20 and the axial bearing 18, 19 set the support element 17 into a suspended state relative to the support element 16 for magnetic bearing.

An additional rotation of the support element 17 around the tilt axis K, relative to the support element 16, takes place with the aid of the described electromagnetic drive means which are presently integrated into the radial bearing 20. In this situation, the electromagnets 38 of the magnetic brake 36 are operated such that, by generating a corresponding magnetic field, they hold the flange 37 at a defined distance from the brake ring 40. To fix or, respectively, arrest the support element 17 relative to the support element 16, the current to the electromagnets 38 is deactivated. The flange 37 is thereupon attracted by the permanent magnet 24 of the radial bearing 20 and pressed against the brake covering 41 of the brake ring 40. The magnetic brake 36 can be released again in that the electromagnets 38 or their coils are accordingly charged with current again.

The bearing and drive unit 15 that was schematically presented in FIG. 1 was described in the preceding. In order to be able to pan the stationary part 3 and the rotatable part 4 around the tilt axis K, the computed tomography apparatus 1 requires at least one second bearing unit 115. This bearing unit 115 does not necessarily need to have drive means and a magnetic brake. However, the bearing unit has at least one magnetic radial bearing and at least one magnetic axial bearing. However, the bearing unit 115 can also be designed like the bearing and drive unit 15. In this case, the drive for the tilting or, respectively, pivoting movement of the stationary part 3 and the rotatable part 4 around the tilt axis K, as well as the fixing of the stationary part 3 and the rotatable part 4 relative to the pedestal 5, take place on both sides. Corresponding control and regulatory means (in the form of a computer 42 operated with a corresponding software) that are connected with the bearing and drive unit 15 and the bearing unit 115 are schematically illustrated in FIG. 1.

The tilting of the stationary part 3 and the rotatable part 4 relative to the pedestal 5 preferably takes place in an angle range of +/−1° around the tilt axis K from the initial position shown in FIG. 1.

FIG. 5 shows a section representation of a second exemplary embodiment of a bearing and drive unit 215 which differs from the bearing and drive unit 15 to the effect that the radial bearing 200 and the electromagnetic drive unit 300 are separate from one another and are arranged offset relative to one another in the direction of the tilt axis K. Moreover, the bearing and drive unit 215 has a support bearing 400. The remaining components of the bearing and drive unit 215 corresponding in design and function, as necessary with dimensions adapted to the structural shape of said bearing and drive unit 215, to the components of the bearing and drive unit 15, which is why these are provided with the same reference characters.

In the exemplary embodiment of the invention that is shown in FIG. 5, the radial bearing 200 is arranged in a first plane E1 and—like the radial bearing 20 integrated with an electromagnetic drive—has a radially outward, annular radial arrangement 21 of electromagnets 22 and a radially inward, annular radial arrangement 23 of permanent magnets 24.

The electromagnetic drive unit 300 is arranged in a plane E2, offset relative to the plane E1 in the direction of the tilt axis K, and likewise has a radially outward, annular radial arrangement 321 of electromagnets 22 and a radially inward, annular radial arrangement 323 of permanent magnets 24.

In contrast to the radial bearing 20 integrated with an electromagnetic drive, all electromagnets 22 and permanent magnets 24 of the radial bearing 200 are provided for the magnetic bearing. Furthermore, all electromagnets 22 and permanent magnets 24 of the electromagnetic drive unit 300 are provided for electromagnetic driving.

As noted, the bearing and drive unit 215 additionally has a support bearing 400 in the form of a conventional roller bearing. The support bearing 400 takes over the support function in the bearing and drive unit 215 if the magnetic field generated by the electromagnets becomes too weak (for example in the event of a power failure). Damage to the magnet bearing of the bearing and drive unit 215 is also avoided in this way. In order to fulfill this purpose, the width of the column 120 between the support bearing 400 arranged at the support el 16 and the support el 17 is smaller than the radial bearing gap 121 and smaller than the drive gap 123. In normal operation, the support bearing 400 attached to the annular support element 16 does not contact the annular support element 17. Only in the event of an error does the support bearing 400 contact the annular support element 17 and take over the support function, whereby a damage to the radial bearing 200 and the electromagnetic drive unit 300 is avoided.

Given a power failure, the magnetic brake 36 is designed such that the flange 37 is attracted by the permanent magnet 24 and is thus pressed against the brake lining 41, so immobilization takes place.

Additionally or alternatively, the device or the computed tomography apparatus can have an uninterruptible power supply 124 as this is indicated in FIG. 1. As is shown for the bearing and drive unit 15 and for the bearing unit 115, a support bearing is not necessary since the power and voltage supply for the magnetic bearing is ensured by the uninterruptible power supply 124 in the event of a power outage.

As noted, the bearing and drive unit 215 can replace the bearing and drive unit 15 and/or the bearing and drive unit 115.

Although modifications and changes may be suggested by those skilled in the art, it is the intention of the inventors to embody within the patent warranted heron all changes and modifications as reasonably and properly come within the scope of their contribution to the art.

We claim as our invention:

1. A device to support and tilt a gantry of a computed tomography apparatus relative to a pedestal, said device comprising:
    a first gantry part and a second gantry part, said first gantry part being rotationally mounted in said second gantry part so as to rotate in a plane in said second gantry part, around a system axis that proceeds perpendicularly through said plane;
    a tilt axle comprising a first tilt axle part attached at opposite ends thereof to opposite sides of said second gantry part, said tilt axle further comprising a second tilt axle part that annularly surrounds said first tilt axle part with a separation therebetween, and that is attached to said pedestal;
    a magnetic bearing configured to magnetically support said second tilt axle part relative to said first tilt axle part, and thereby also support said second gantry part relative to said pedestal; and
    an electromagnetic drive configured to electromagnetically tilt said second gantry part, and thus also said first gantry part and said plane, relative to said pedestal of said gantry around a tilt axis that proceeds through said tilt axle and that proceeds perpendicularly to said system axis.

2. A device as claimed in claim 1 wherein said magnetic bearing comprises at least one magnetic bearing component selected from the group consisting of permanent magnets, electromagnets, and elements composed of ferromagnetic material, and wherein said electromagnetic drive comprises at least one electromagnet.

3. A device as claimed in claim 1 wherein said magnetic bearing comprises at least one magnetic radial bearing that radially supports said second tilt axle part relative to said first tilt axle part, and wherein at least one of said at least one radial bearing and said electromagnetic drive is comprised of a first, radially outlying annular radial arrangement of components selected from the group consisting of permanent magnets, electromagnets, and elements composed of ferromagnetic material, said first, radially outlying annular radial arrangement being mechanically associated with said pedestal of said gantry, and wherein said at least one of said at least one of said radial bearing and said electromagnetic drive comprises a second, radially inward, annular radial arrangement comprised of components selected from the group consisting of permanent magnets, electromagnets, and elements composed of ferromagnetic material, said second, radially inward, annular radial arrangement being mechanically associated with said tiltable part of said gantry, and wherein an annular radial separation exists between said first and second annular radial arrangements.

4. A device as claimed in claim 3 comprising a measurement unit configured to determine a change of a width of said annular radial separation.

5. A device as claimed in claim 4 wherein said measurement unit comprises at least one measurement component selected from the group consisting of Hall sensors, inductive sensors, and capacitive sensors.

6. A device as claimed in claim 4 wherein said magnetic radial bearing comprises a plurality of electromagnets, each having a coil exhibiting an inductance, and wherein said measurement unit comprises a component configured to determine said change of said width of said annular radial gap by detecting a change in the inductance of at least one of the respective coils of said plurality of electromagnets.

7. A device as claimed in claim 1 wherein said magnetic bearing comprises at least one magnetic axial bearing that axially supports said second tilt axle part relative to said first tilt axle part, comprised of a first axial arrangement of components selected from the group consisting of permanent magnets, electromagnets, and elements composed of ferromagnetic material, said first axial arrangement being mechanically associated with said pedestal of said gantry, and a second, axial arrangement that is axially spaced from said first axial arrangement along said system axis and that is comprised of components selected from the group consisting of permanent magnets, electromagnets, and elements composed of ferromagnetic material, said second axial arrangement being mechanically associated with said tiltable part of said gantry, and wherein an annular axial separation exists between said first and second axial arrangements.

8. A device as claimed in claim 7 comprising a measurement unit configured to determine a change of a width of said annular axial separation.

9. A device as claimed in claim 8 wherein said measurement unit comprises at least one measurement component selected from the group consisting of Hall sensors, inductive sensors, and capacitive sensors.

10. A device as claimed in claim 8 wherein said magnetic axial bearing comprises a plurality of electromagnets, each having a coil exhibiting an inductance, and wherein said measurement unit comprises a component configured to determine said change of said width of said annular axial gap by detecting a change in the inductance of at least one of the respective coils of said plurality of electromagnets.

11. A device as claimed in claim 1 wherein said magnetic bearing comprises a magnetic radial bearing that radially supports said second tilt axle part relative to said first tilt axle part, located in a first plane that is perpendicular to said tilt axis, and wherein said electromagnetic drive is located in a second plane that is perpendicular to said tilt axis and that is spaced from said first plane along said tilt axis.

12. A device as claimed in claim 1 wherein said magnetic bearing comprises a magnetic radial bearing that radially supports said second tilt axle part relative to said first tilt axle part, and wherein said electromagnetic drive is integrated into said magnetic radial bearing.

13. A device as claimed in claim 12 wherein said radial bearing with said electromagnetic drive integrated therein comprises a first, radially outward, annular radial arrangement of electromagnets mechanically associated with said pedestal of said gantry, and a second, radially inward, annular radial arrangement comprising components selected from the group consisting of permanent magnets and elements composed of ferromagnetic material, mechanically associated with said tiltable part of said gantry, and a control computer configured to operate said electromagnets to produce a rotating electromagnetic field that rotates around said tilt axis to electromagnetically tilt said tiltable part of said gantry relative to said pedestal of said gantry.

14. A device as claimed in claim 13 wherein said electromagnets are divided into groups respectively forming segments of a circle around said stationary part, and wherein said control computer is configured to control the respective groups of electromagnets to produce said rotating electromagnetic field.

15. A device as claimed in claim 12 wherein said magnetic radial bearing with said electromagnetic drive integrated therein comprises a first, radially outward, annular radial arrangement of components selected from the group consisting of permanent magnets and elements composed of ferromagnetic material, mechanically associated with said pedestal, and a second, radially inward, annular radial arrangement of electromagnets mechanically associated with said tiltable part, and a control computer configured to operate said electromagnets to produce a rotating electromagnetic field that rotates around said tilt axis to electromagnetically tilt said pedestal part of said gantry relative to said pedestal of said gantry.

16. A device as claimed in claim 15 wherein said electromagnets are divided into groups respectively forming segments of a circle around said stationary part, and wherein said control unit is configured to control the respective groups of electromagnets to produce said rotating electromagnetic field.

17. A device as claimed in claim 12 wherein said magnetic radial bearing with said electromagnetic drive integrated therein comprises a first, radially outward, annular radial arrangement of electromagnets mechanically associated with said pedestal, and a second, radially inward, annular radial arrangement of electromagnets mechanically associated with said tiltable part, and a control unit configured to operate said electromagnets to produce a rotating electromagnetic field that rotates around said tilt axis to electromagnetically tilt said tiltable part of said gantry relative to said pedestal of said gantry.

18. A device as claimed in claim 17 wherein said electromagnets are divided into groups respectively forming segments of a circle around said tilt axis, and wherein said control computer is configured to control the respective groups of electromagnets to produce said rotating electromagnetic field.

19. A device as claimed in claim 1 comprising a roller bearing that mechanically supports said tiltable part relative to said pedestal.

20. A device as claimed in claim 1 comprising an uninterruptable power supply that supplies power at least to said electromagnetic bearing.

21. A computed tomography apparatus comprising:
a first gantry part and a second gantry part, said first gantry part being rotationally mounted in said second gantry part so as to rotate in a plane in said second gantry part, around a system axis that proceeds perpendicularly through said plane;
a tilt axle comprising a first tilt axle part attached at opposite ends thereof to opposite sides of said second gantry part, said tilt axle further comprising a second tilt axle part that annularly surrounds said first tilt axle part with a separation therebetween, and that is attached to said pedestal;
an x-ray radiator and an x-ray radiation detector mounted on said first gantry part at opposite sides of said system axis;
a magnetic bearing configured to magnetically support said second tilt axle part relative to said first tilt axle part, and thereby also support said second gantry part relative to said pedestal; and
an electromagnetic drive configured to electromagnetically tilt said second gantry part, and thus also said first gantry part and said plane, relative to said pedestal of said gantry around a tilt axis that proceeds through said tilt axle and that proceeds perpendicularly to said system axis; and
a control computer configured to operate said x-ray radiator and said x-ray radiation detector to acquire computed tomography data.

22. A computed tomography apparatus as claimed in claim 21 wherein said magnetic bearing comprises at least one magnetic bearing component selected from the group consisting of permanent magnets, electromagnets, and elements composed of ferromagnetic material, and wherein said electromagnetic drive comprises at least one electromagnet.

23. A computed tomography apparatus as claimed in claim 21 wherein said magnetic bearing comprises at least one magnetic radial bearing that radially supports said second tilt axle part relative to said first tilt axle part, and wherein at least one of said at least one magnetic radial bearing and said electromagnetic drive is comprised of a first, radially outlying annular radial arrangement of components selected from the group consisting of permanent magnets, electromagnets, and elements composed of ferromagnetic material, said first, radially outlying annular radial arrangement being mechanically associated with said pedestal of said gantry, and wherein said at least one of said at least one of said magnetic radial bearing and said electromagnetic drive comprises a second, radially inward, annular radial arrangement comprised of components selected from the group consisting of permanent magnets, electromagnets, and elements composed of ferromagnetic material, said second, radially inward, annular radial arrangement being mechanically associated with said tiltable part of said gantry, and wherein an annular radial separation exists between said first and second annular radial arrangements.

24. A computed tomography apparatus as claimed in claim 23 comprising a measurement unit configured to determine a change of a width of said annular radial separation.

25. A computed tomography apparatus as claimed in claim 24 wherein said measurement unit comprises at least one measurement component selected from the group consisting of Hall sensors, inductive sensors, and capacitive sensors.

26. A computed tomography apparatus as claimed in claim 24 wherein said magnetic radial bearing comprises a plurality of electromagnets, each having a coil exhibiting an inductance, and wherein said measurement unit comprises a component configured to determine said change of said width of said annular radial gap by detecting a change in the inductance of at least one of the respective coils of said plurality of electromagnets.

27. A computed tomography apparatus as claimed in claim 21 wherein said magnetic bearing comprises at least one magnetic axial bearing that axially supports said second tilt axle part relative to said first tilt axle part, comprised of a first axial arrangement of components selected from the group consisting of permanent magnets, electromagnets, and elements composed of ferromagnetic material, said first axial arrangement being mechanically associated with said pedestal of said gantry, and a second, axial arrangement that is axially spaced from said first axial arrangement along said system axis and that is comprised of components selected from the group consisting of permanent magnets, electromagnets, and elements composed of ferromagnetic material, said second axial arrangement being mechanically associated with said tiltable part of said gantry, and wherein an annular axial separation exists between said first and second axial arrangements.

28. A computed tomography apparatus as claimed in claim 27 comprising a measurement unit configured to determine a change of a width of said annular axial separation.

29. A computed tomography apparatus as claimed in claim 27 wherein said measurement unit comprises at least one measurement component selected from the group consisting of Hall sensors, inductive sensors, and capacitive sensors.

30. A computed tomography apparatus as claimed in claim 28 wherein said magnetic axial bearing comprises a plurality of electromagnets, each having a coil exhibiting an inductance, and wherein said measurement unit comprises a component configured to determine said change of said width of said annular axial gap by detecting a change in the inductance of at least one of the respective coils of said plurality of electromagnets.

31. A computed tomography apparatus as claimed in claim 21 wherein said magnetic bearing comprises a magnetic radial bearing that radially supports said second tilt axle part relative to said first tilt axle part, located in a first plane that is perpendicular to said tilt axis, and wherein said electromagnetic drive is located in a second plane that is perpendicular to said tilt axis and that is spaced from said first plane along said tilt axis.

32. A computed tomography apparatus as claimed in claim 21 wherein said magnetic bearing comprises a magnetic radial bearing that radially supports said second tilt axle part relative to said first tilt axle part, and wherein said electromagnetic drive is integrated into said magnetic radial bearing.

33. A computed tomography apparatus as claimed in claim 32 wherein said radial bearing with said electromagnetic drive integrated therein comprises a first, radially outward, annular radial arrangement of electromagnets mechanically associated with said pedestal of said gantry, and a second, radially inward, annular radial arrangement comprising components selected from the group consisting of permanent magnets and elements composed of ferromagnetic material, mechanically associated with said tiltable part of said gantry, and wherein said control computer is configured to operate said electromagnets to produce a rotating electromagnetic field that rotates around said tilt axis to electromagnetically tilt said tiltable part of said gantry relative to said pedestal of said gantry.

34. A computed tomography apparatus as claimed in claim 33 wherein said electromagnets are divided into groups respectively forming segments of a circle around said stationary part, and wherein said control computer is configured to control the respective groups of electromagnets to produce said rotating electromagnetic field.

35. A computed tomography apparatus as claimed in claim 32 wherein said magnetic radial bearing with said electromagnetic drive integrated therein comprises a first, radially outward, annular radial arrangement of components selected from the group consisting of permanent magnets and elements composed of ferromagnetic material, mechanically associated with said pedestal, and a second, radially inward, annular radial arrangement of electromagnets mechanically associated with said tiltable part, and a control computer configured to operate said electromagnets to produce a rotating electromagnetic field that rotates around said tilt axis to electromagnetically tilt said pedestal part of said gantry relative to said pedestal of said gantry.

36. A computed tomography apparatus as claimed in claim 35 wherein said electromagnets are divided into groups respectively forming segments of a circle around said tilt axis, and wherein said control unit is configured to control the respective groups of electromagnets to produce said rotating electromagnetic field.

37. A computed tomography apparatus as claimed in claim 32 wherein said magnetic radial bearing with said electromagnetic drive integrated therein comprises a first, radially outward, annular radial arrangement of electromagnets mechanically associated with said pedestal, and a second, radially inward, annular radial arrangement of electromagnets mechanically associated with said tiltable part, and wherein said control computer is to operate said electromagnets to produce a rotating electromagnetic field that rotates around said tilt axis to electromagnetically tilt said tiltable part of said gantry relative to said pedestal of said gantry.

38. A computed tomography apparatus as claimed in claim 37 wherein said electromagnets are divided into groups respectively forming segments of a circle around said tilt axis, and wherein said control computer is configured to control the respective groups of electromagnets to produce said rotating electromagnetic field.

39. A computed tomography apparatus as claimed in claim 21 comprising a roller bearing that mechanically supports said tiltable part relative to said pedestal.

40. A computed tomography apparatus as claimed in claim 21 comprising an uninterruptable power supply that supplies power at least to said electromagnetic bearing.

41. A device as claimed in claim 1 wherein said magnetic bearing is a magnetic radial bearing that radially supports said second tilt axle part relative to said first tilt axle part, and wherein said device comprises:
  a plurality of magnetic components, said plurality extending completely around said tilt axis in respective annular gaps between second tilt axle part and the first tilt axle part, with all of said magnetic components situated in a plane that is perpendicular to said tilt axis;
  said magnetic radial bearing comprising a first sub-plurality of said plurality of magnetic components and said electromagnetic drive comprising a second sub-plurality of said plurality of magnetic components, with no magnetic component in said plurality of magnetic components being in both said first sub-plurality and in said second sub-plurality; and
  the magnetic components in said first sub-plurality alternating around said annular gap in said plane with the magnetic components in said second sub-plurality.

42. A device as claimed in claim 41 wherein the magnetic components in said first sub-plurality alternate around said annular gap in said plane with the magnetic components in said second sub-plurality with every magnetic component in said first sub-plurality being between two magnetic components in said second sub-plurality and every magnetic component in said second sub-plurality being between two magnetic components in said first sub-plurality.

43. A device as claimed in claim 41 wherein said magnetic components in said first sub-plurality alternate in angular sectors in said plane around said system axis with magnetic components in different angular sectors in said second sub-plurality, with each angular sector comprising only magnetic components in said first sub-plurality or only magnetic components in said second sub-plurality.

44. A device as claimed in claim 43 wherein each angular sector encompasses 60° of said annular gap in said plane.

45. A device as claimed in claim 43 wherein each angular sector encompasses 45° of said annular gap in said plane.

46. A computed tomography apparatus as claimed in claim 1 wherein said magnetic bearing is a magnetic radial bearing that radially supports said second tilt axle part relative to said first tilt axle part, and wherein said computed tomography apparatus comprises:
  a plurality of magnetic components, said plurality extending completely around said tilt axis in respective annular gaps between said second tilt axle part and the first tilt axle part, with all of said magnetic components situated in a plane that is perpendicular to said system axis;
  said magnetic radial bearing comprising a first sub-plurality of said plurality of magnetic components and said electromagnetic drive comprising a second sub-plurality of said plurality of magnetic components, with no magnetic component in said plurality of magnetic components being in both said first sub-plurality and in said second sub-plurality; and
  the magnetic components in said first sub-plurality alternating around said annular gap in said plane with the magnetic components in said second sub-plurality.

47. A computed tomography apparatus as claimed in claim 46 wherein the magnetic components in said first sub-plurality alternate around said annular gap in said plane with the magnetic components in said second sub-plurality with every magnetic component in said first sub-plurality being between two magnetic components in said second sub-plurality and every magnetic component in said second sub-plurality being between two magnetic components in said first sub-plurality.

48. A computed tomography apparatus as claimed in claim 46 wherein said magnetic components in said first sub-plurality alternate in angular sectors in said plane around said system axis with magnetic components in different angular sectors in said second sub-plurality, with each angular sector comprising only magnetic components in said first sub-plurality or only magnetic components in said second sub-plurality.

49. A computed tomography apparatus as claimed in claim 48 wherein each angular sector encompasses 60° of said annular gap in said plane.

50. A computed tomography apparatus as claimed in claim 48 wherein each angular sector encompasses 45° of said annular gap in said plane.

* * * * *